United States Patent
Baveas (10) Patent No.: US 12,178,967 B2
(45) Date of Patent: Dec. 31, 2024

(54) THERAPEUTIC OR PLAY DEVICE AND METHOD OF USE

(71) Applicant: Dimitra Baveas, Brisbane (AU)

(72) Inventor: Dimitra Baveas, Brisbane (AU)

(*) Notice: Subject to any disclaimer, the term of this patent is extended or adjusted under 35 U.S.C. 154(b) by 0 days.

(21) Appl. No.: 16/490,471

(22) PCT Filed: Feb. 28, 2018

(86) PCT No.: PCT/AU2018/050181
§ 371 (c)(1),
(2) Date: Aug. 30, 2019

(87) PCT Pub. No.: WO2018/157205
PCT Pub. Date: Sep. 7, 2018

(65) Prior Publication Data
US 2020/0261686 A1     Aug. 20, 2020

(30) Foreign Application Priority Data

Mar. 3, 2017   (AU) ................................ 2017900734

(51) Int. Cl.
*A61M 21/00*   (2006.01)

(52) U.S. Cl.
CPC . *A61M 21/0094* (2013.01); *A61M 2021/0022* (2013.01); *A61M 2021/0027* (2013.01); *A61M 2021/0044* (2013.01); *A61M 2205/0216* (2013.01)

(58) Field of Classification Search
CPC ...... A61M 21/0094; A61M 2021/0022; A61M 2021/0027; A61M 2021/0044; A61M 2205/0216; A61F 5/3776; A61F 5/37; A47D 15/02; A47D 15/008
USPC .............. 5/494, 498, 500, 502, 628; 24/72.5
See application file for complete search history.

(56) References Cited

U.S. PATENT DOCUMENTS

| | | | | |
|---|---|---|---|---|
| 4,241,466 A | * | 12/1980 | Mendyk | A47G 9/02 5/500 |
| 4,488,323 A | * | 12/1984 | Colburn | A47G 9/0238 5/923 |
| 4,653,131 A | * | 3/1987 | Diehl | A47C 21/08 128/872 |
| 4,941,453 A | * | 7/1990 | Shakas | A47D 9/02 D6/390 |
| 5,014,376 A | | 5/1991 | Doran et al. | |
| 5,049,145 A | * | 9/1991 | Flug | A61F 13/622 24/442 |
| 5,086,530 A | * | 2/1992 | Blake | A47C 31/105 5/500 |

(Continued)

FOREIGN PATENT DOCUMENTS

GB    2522687 A    8/2015

OTHER PUBLICATIONS

Capmor "How to Mate Two Sleeping Bags Together" accessed online at https://outdoors.campmor.com/mate-two-sleeping-bags-together/ (Year: 2015).*

(Continued)

*Primary Examiner* — Thaddeus B Cox
(74) *Attorney, Agent, or Firm* — WOMBLE BOND DICKINSON (US) LLP (57) ABSTRACT

A therapeutic or play device that provides a user with a sense of spatial orientation and/or sensory feedback or input such as people with autism/sensory processing disorders.

12 Claims, 3 Drawing Sheets

(56) References Cited

U.S. PATENT DOCUMENTS

| | | | | |
|---|---|---|---|---|
| 5,439,008 | A * | 8/1995 | Bowman | A47D 15/001 |
| | | | | 128/845 |
| 5,623,950 | A | 4/1997 | Bergeron | |
| 5,735,003 | A * | 4/1998 | Judge | A47G 9/086 |
| | | | | 5/413 AM |
| 5,970,541 | A | 10/1999 | Chiang | |
| 6,513,164 | B1 * | 2/2003 | Hearns | A47D 15/008 |
| | | | | 5/904 |
| 6,684,422 | B2 | 2/2004 | Lefevre et al. | |
| 2003/0154549 | A1 * | 8/2003 | Landry | A47D 15/02 |
| | | | | 5/923 |
| 2004/0049850 | A1 * | 3/2004 | Li | A47D 15/02 |
| | | | | 5/482 |
| 2007/0028383 | A1 * | 2/2007 | Mehrotra | A47G 9/0253 |
| | | | | 5/490 |
| 2007/0113352 | A1 * | 5/2007 | Poulos | A61G 7/05784 |
| | | | | 5/727 |
| 2007/0180625 | A1 * | 8/2007 | Walke | A61G 7/0504 |
| | | | | 5/706 |
| 2008/0099060 | A1 | 5/2008 | Stocking et al. | |
| 2009/0044337 | A1 | 2/2009 | McKee | |
| 2009/0294075 | A1 * | 12/2009 | Huck | A63H 33/008 |
| | | | | 160/382 |
| 2011/0061701 | A1 * | 3/2011 | Perez | A47C 29/003 |
| | | | | 135/96 |
| 2013/0067660 | A1 * | 3/2013 | Sloan | A47D 15/02 |
| | | | | 5/494 |
| 2016/0324342 | A1 * | 11/2016 | Khan | A47G 9/02 |

OTHER PUBLICATIONS

Weiss "Snugpak sleeping bag features built-in LED light" accessed online at https://newatlas.com/snugpak-sleeping-bag-built-in-led-light/22394/ (Year: 2012).*

Sensory Matters ("Sensory Matters Lycra Bed Sheet" YouTube, uploaded by Sensory Matters, Nov. 20, 2016, https://www.youtube.com/watch?v= ORuz4HVZa9w) (Year: 2016).*

International Search Report mailed on Jun. 20, 2018 for International Application No. PCT/AU2018/050181 in 2 pages.

* cited by examiner

THERAPEUTIC OR PLAY DEVICE AND METHOD OF USE

CROSS-REFERENCE TO RELATED APPLICATIONS

This patent application is a U.S. National Phase Application under 35 U.S.C. § 371 of International Application No. PCT/AU2018/050181, filed Feb. 28, 2018, which claims the benefit of Australia Patent Application No. 2017900734, filed Mar. 3, 2017, and these applications are hereby incorporated by reference in their entirety.

TECHNICAL FIELD

The present invention relates to therapeutic or play devices and particularly to devices that provide a user with a sense of spatial orientation such as people with autism/sensory processing disorders.

BACKGROUND ART

Sensory processing disorder is a condition in which the brain has trouble receiving and responding to information that comes in through the senses.

Formerly referred to as sensory integration dysfunction, it is not currently recognized as a distinct medical diagnosis.

Some people with sensory processing disorder are oversensitive to things in their environment. Common sounds may be painful or overwhelming. The light touch of a shirt may chafe the skin.

Others with sensory processing disorder may:
Be uncoordinated
Bump into things
Be unable to tell where their limbs are in space
Be hard to engage in conversation or play Sensory processing problems are usually identified in children. But they can also affect adults. Sensory processing problems are commonly seen in developmental conditions like autism spectrum disorder.

Various solutions or treatment regimes have been proposed in the past, including a variety of different devices such as that disclosed in U.S. Pat. No. 6,086,551 which discloses a flexible compression and stabilising orthotic in the form of a bodysuit or that in United States Patent Application No. 20120110736 which discloses a pouch blanket with no ends (a tubular shape) which wraps entirely about a mattress and is anchored with the weight of the mattress and the individual.

Both of these devices can only be used in particular situations and both have drawbacks. For example, an individual using the orthotic from U.S. Pat. No. 6,086,551 must don and doff the orthotic which is difficult and time consuming given its close fit and resilient nature meaning that it is not particularly useful for shorter sessions of use. Similarly the device in United States Patent Application No. 20120110736 is expressly for use with a mattress and therefore, will not find use in situations where a bed or mattress is not readily available such in outside play or classroom situations.

It will be clearly understood that, if a prior art publication is referred to herein, this reference does not constitute an admission that the publication forms part of the common general knowledge in the art in Australia or in any other country.

SUMMARY OF INVENTION

The present invention is directed to a therapeutic or play device and method of use, which may at least partially overcome at least one of the abovementioned disadvantages or provide the consumer with a useful or commercial choice.

With the foregoing in view, the present invention in one form, resides broadly in a therapeutic or play device including a substantially planar, resilient, flexible sheet of material with at least one attachment mechanism provided at least partially along at least a pair of portions to allow the flexible sheet of material to be attached relative to a surface to form a restricting or confining volume with an entry/exit requiring at least partial deformation of the flexible sheet for entry and exit.

The toy or aide used to improve proprioception, coordination and sensory processing. Through the additional sensory input students with sensory processing problems, autism and many other learning issues can improve their ability to learn, maintain focus and cooperate. The device can be used in the setting as a break and then return to focus or it can be used to help the user maintain focus in an activity. It increases participation by the user in a variety of public and private settings including but not limited to classrooms, clinics, homes, early childhood settings and mental health care facilities etc. It can be used with one user or more than one.

The therapeutic or play device of the present invention can be used for therapy, play or a mixture of therapy disguised by play.

The device of the present invention will typically have an upper side and a lower side although the sides are really only defined once the device of the present invention is attached relative to the surface.

The device of the present invention includes a substantially planar, resilient, flexible sheet of material. The sheet of material may be any shape although a rectangular shape will normally be preferred.

The sheet of material may have any size. The particular size of the sheet of material will normally be dependent upon the needs of the user. The sheet of material may be relatively small say approximately 1 m×1 m or may be larger for example between 1 to 2 m in width and 2 to 4 m in length. The different sizes of device will typically provide different functionality. For example, the smaller devices will typically be used to provide a user with sensory feedback from positioning themselves at least partially underneath the device when attached relative to the surface whereas the larger devices may be used for additional purposes such as play beneath the device. Size can also depend on the size of the intended user e.g. toddlers may want a small size and adults may require a larger size.

The sheet of material included in the device of the present invention is typically resilient. In a preferred form, the sheet of material is preferably resilient in multiple directions. Any suitable material or combination of materials may be used to form the sheet of the present invention. It is particularly preferred that the material used is one or more fabrics. Different materials or surfaces may be provided on the same device. For example, an underside of the sheet of material may be provided in a different configuration to an upper side of the sheet of material in order to provide different sensory feedback on the different sides. One or more different materials may be used over the length of the sheet of material and/or one or more different materials may be used over the width of the sheet of material.

The degree of resilience of the sheet material of the present invention may be adjusted or selected through an appropriate choice of material or combination of materials. The material will typically be chosen to provide the required or desired functionality. For example, the main purpose of the device is to provide sensory feedback and therefore, one or more materials may be chosen to provide a particular sensory effect. The material or materials chosen may provide sensory feedback in the form of touch, sight and/or sound or combinations of these particular senses. It is preferred that no sensory effect is provided in terms of smell although this may be possible through an appropriate material choice or through the application of odour materials to the device but particularly not taste. Sensory feedback may be provided in the form of touch by changing the types of materials in terms of surface roughness or finish, for sight the material or materials chosen may have particular visual features either inherent in the manufacture of the materials or applied to the form of shapes or patterns or other visual features and in terms of sound, the materials chosen may make one or more sounds when stimulated such as a ridged material which may make a sound when the user rubs their fingers over it or crinkle paper which makes a crunching sound when touched. Additionally, the type of material and the colour chosen may allow varying degrees of light through the material. These are examples only and any form of material may be provided to achieve a particular sensory effect.

In a particularly simple preferred form, the sheet of material will be a single unitary sheet made from spandex or lycra based material but more than one sheet of material may be used. Preferably, the sheet of material will be flexible in order to allow a user to move beneath the sheet of material when attached relative to a surface.

Preferably, the flexible sheet of material is formed from a multidirectional resilient material. In a preferred embodiment, the material is a 20:80 blend of Lycra° and nylon although different blends can and typically will be used to adjust the compression load of the device.

More than one planar sheet may be attached together in order to define the shape for example a three-dimensional shape such as a tunnel or a tent or an enclosure or even amaze for example. When provided in a planar sheet embodiment, the planar sheet may be used to connect to or to connect one or more three-dimensional shapes to allow a user to travel from the one enclosure through or under the device of the present invention to another enclosure.

In a preferred embodiment of the present invention, a base may be provided relative to which the substantially planar, resilient, flexible sheet of material can be attached. The base may be or provide a surface relative to which the flexible sheet of material can be attached. The base may be configured as a mat for example. The base may have a cushioning effect in order to make the base more comfortable for a user to crawl on or lie on. For example, the base may be formed of a foamed material, a memory foam material or may be inflatable for example. The base may provide a sensory effect or further sensory feedback itself in addition to the flexible sheet of material. In particular, the base may be provided with/chosen for/configured to provide one or more sensory qualities or effects to increase or decrease sensory input for a user.

The base may be provided with one or more attachment mechanisms in order to attach the attachment mechanism is provided on the sheet of material. It is preferred that the base is provided with an attachment mechanism which allows attachment of the preferred sheet of material relative thereto and the attachment mechanism will normally be incorporated into or used on the base.

The base may provide the planar sheet of material with the ability to be used both indoor and outdoor. For example, a lower surface of the base may be provided in a waterproof embodiment in order to allow the base to be used on grass for example.

The base will preferably be generally planar but may be shaped. For example, the base may include or may be provided with shaped blocks or integrated shapes provided on the base or attachable relative thereto which can then be covered by the substantially planar sheet of material.

The device of the present invention also includes an attachment mechanism provided at least partially along at least a pair of portions of the flexible sheet of material to allow the flexible sheet of material to be attached relative to a surface to form a restricting or confining volume with an entry/exit requiring at least partial the formation of the flexible sheet for entry and exit.

Any type of attachment mechanism can be used. However, it is preferred that an attachment mechanism which is fast, easy to operate, potentially even with limited tactile skills or grip strength and one which is releasable easily with determined removal but much less easily with accidental removal.

In a particularly preferred embodiment, the attachment mechanism used on the device of the present invention will be a hook portion such as the hook portion from a Velcro fastening system. The hook portion is preferably usable to attach the device relative to floor surfaces such as carpeted floor surfaces. In an alternative embodiment, other systems such as magnets for example may be used but this is not as utilitarian as the hook portion from a Velcro fastening system.

A corresponding portion of the Velcro fastening system, the loop portion may be provided on or relative to the surface. Where the surface is provided as a base, the loop portion may be provided on or relative to the base.

The attachment mechanism extends at least partially along at least a pair of portions. The attachment mechanism may not need to extend continuously along at least a pair of portions and for example, the attachment mechanism may include a number of spaced apart attachment portions.

It is preferred that the attachment mechanism is provided at or adjacent to a pair of side edges of the preferred embodiment of a substantially rectangular sheet of material but this is not necessarily required. One or more intermediate portions may be provided between an outer pair of attachment portions in order to form "lanes" on the device. An attachment portion may be provided at an end of the preferred embodiment of a substantially rectangular sheet of material but preferably not at both ends as this may create anxiety on the part of the user because it may make them feel trapped.

In one preferred embodiment, one or more shaped entryway portions may be provided at an entry/exit of the device in order to hold the entry/exit open for access. Where provided, an entryway portion may have any shape but will preferably be a substantially rigid shape about which a portion of the sheet of material can be preferably releasably attached, such as by using Velcro or similar, in order to hold the entry/exit open, that is, raised above the surface relative to which the device is attached. One or more poles or other device(s) may be positioned and/or attached at any point under the sheet of material to raise it giving it a more tent like effect. If a base is provided, the one or more poles or other device(s) may be attached or mounted to, or relative to the base.

The device may include one or more holes in the material. For example, a hole in the sheet could allow a user to stick their head through providing further comfort for the user and/or to allow monitoring of the user whilst under/in the device.

The device may include one or more pockets or an attachment mechanism onto the sheet of material in order to allow a user to locate items of educational or intrinsic value, for example a sensory toy/letters or words or similar that can also be attached to the material or base and be located or removed by the user.

One or more lights or luminescent portion may be provided on one or more sides of the sheet of material or on the base.

In use, the product is fixed to a surface allowing for variability of resistance depending on what is required (less or more resistance). The user can go under it to utilise this resistance or the top side can also be used if the user receives positive sensory feedback from being on the top of it. Primarily its use is for the user to go under between the material and the surface to receive additional proprioceptive input and move, play or lie under it. To begin with the design is that of a tunnel (either rectangle or square shape) with quick release mechanisms, at the moment with a hook/loop attached on either side. It can be sold with or without a base as there are a multitude of common base options e.g. loop carpet tiles can be utilised. It can be positioned horizontally or vertically.

In an alternative form, the present invention resides in a method of using a therapeutic or play device, the therapeutic or play device including a substantially planar, resilient, flexible sheet of material with an attachment mechanism provided at least partially along at least a pair of portions, and attaching the flexible sheet of material relative to a surface to form a restricting or confining volume with an entry/exit requiring at least partial deformation of the flexible sheet for entry and exit.

As mentioned above, although the flexible sheet of material may be attached relative to a surface or a base, in normal use, the flexible sheet will be attached to or relative to a ground surface, preferably a carpeted floor for example.

Educators, therapists, and parents and the like will be able to fulfil the sensory and movement needs of users without being intrusive and without utilising any form of restrictive practice or needing to leave the setting. The user will choose to stay in the space rather than leave the space because they find using the product intrinsically satisfying. When they leave the setting to fulfil their sensory/movement needs it not only creates problems with supervision and safety it is more difficult for the user to return to the setting and they further miss out on being exposed to further knowledge and valuable experiences. By having access to a product that is fixed in the setting it gives the user greater access to the social, communication, education and other benefits of being in that space.

When a Lycra® or similar tunnel is used, supervisors and/or facilitators may also hold the ends so that the user can move through it.

The temporarily fixed position of the device provides a multitude of benefits and yet it is easily positioned and it is easily changed or removed. The device of the present invention can be positioned onto any surface and takes up very little space and it is easily positioned and repositioned depending on the users and/or facilitators needs.

The device provides increased proprioceptive input assists in the development of the user's sensory development, sensory motor development, perceptual motor development, cognition and core muscle strength. Users can crawl through the restricted or confined volume improving their reflexive movement/strength or play under it, or simply lie under it.

The amount of resistance placed on the user is dependent upon the amount required by the user/users and can be adjusted quickly and easily. Access to users under the device can be quickly achieve if necessary simply by detachment of the device from the surface, at least partially or fully. In other words, the attachment mechanisms can be moved to make the device either loose on the ground or taut relative to the ground surface, and there may be portions of the device which are loose and then other portions of the device, which are taut, as required by the user.

It can be used in structured lessons or free play in any number of settings.

It can be used in cooperation with other users or individually.

In some embodiments, other attachment assemblies may be provided to allow the device to assume other configurations. For example, one or more attachment assemblies may be provided allowing sides of the device to be attached together making it a tube, which could then be open an both ends or closed on itself to create a toriodal space. There could also be one or more attachment assemblies provided at the end so that the device can function more like a body sock. This would give the product multiple dimensions.

This means that the versatility of the product can be used as a body sock or tunnel that may or may not attach to a surface. This is beneficial because enclosing the device to form a tunnel and then still being able to utilise at least one strip of hook to attach it to a surface means that additional people are not required for the user to be able to crawl through the space without the fabric moving or bunching together. It may be that the one or more attachment assemblies is utilised in such a way that the tunnel is completely enclosed to make a tube and also attached to the surface or just enclosed and not attached creating a more conventional lycra tunnel.

A cover may be used over portions of the one or more attachment assemblies for example the hook (male) Velcro or other type of quick release attachment. Providing an additional side panel of loop Velcro folding over and onto the hook Velcro will protect the material of construction when not in use and also add to the product's functionality.

Although described in terms of a human user, normally a child, the invention may easily be adapted for use with an animal for example calming horses or dogs by providing sensory input for calming effect. The product may be used to encourage movement or to calm by providing proprioceptive input.

Any of the features described herein can be combined in any combination with any one or more of the other features described herein within the scope of the invention.

The reference to any prior art in this specification is not, and should not be taken as an acknowledgement or any form of suggestion that the prior art forms part of the common general knowledge.

BRIEF DESCRIPTION OF DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows.

DESCRIPTION OF EMBODIMENTS

According to a particularly preferred embodiment of the present invention, a therapeutic or play device 10 is provided.

The therapeutic or play device 10 including a substantially planar, resilient, flexible sheet 11 of material with an attachment mechanism 12 provided at least partially along at least a pair of portions to allow the flexible sheet 11 of material to be attached relative to a surface to form a restricting or confining volume with an entry 14 and/or exit 15 requiring at least partial deformation of the flexible sheet 11 for entry and exit.

The therapeutic or play device 10 can be used as a toy or aide used to improve proprioception, coordination and sensory processing. Through the additional sensory input students with sensory processing problems, autism and many other learning issues can improve their ability to learn, maintain focus and cooperate. The device can be used within the setting as a break for the user and then return to focus or it can be used to help the user maintain focus in an activity. It increases participation by the user in a variety of public and private settings including but not limited to classrooms, clinics, homes, early childhood settings and mental health care facilities etc. It can be used with one user or more than one.

Figure 1:
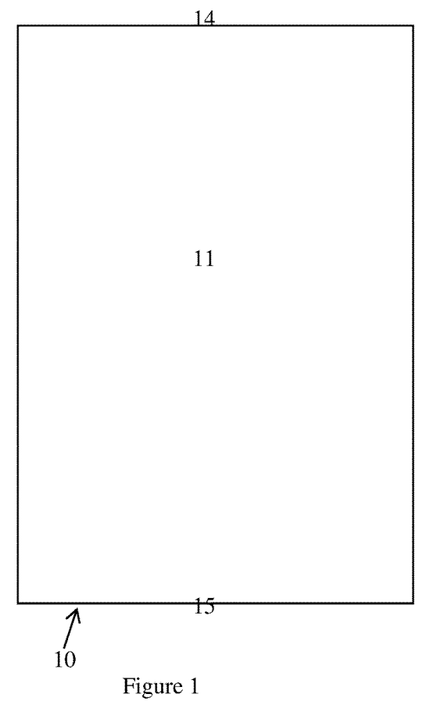
FIG. 1 is a plan view of a therapeutic or play device according to a particularly preferred embodiment of the present invention.
Figure 2:
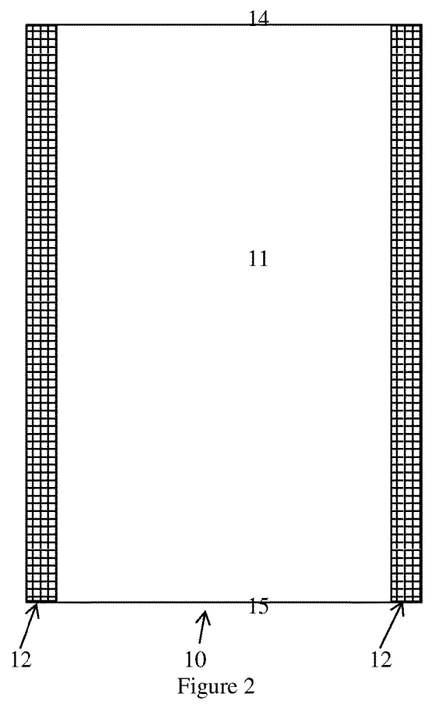
FIG. 2 is a bottom view of the therapeutic or play device illustrated in FIG. 1.
Figure 3:
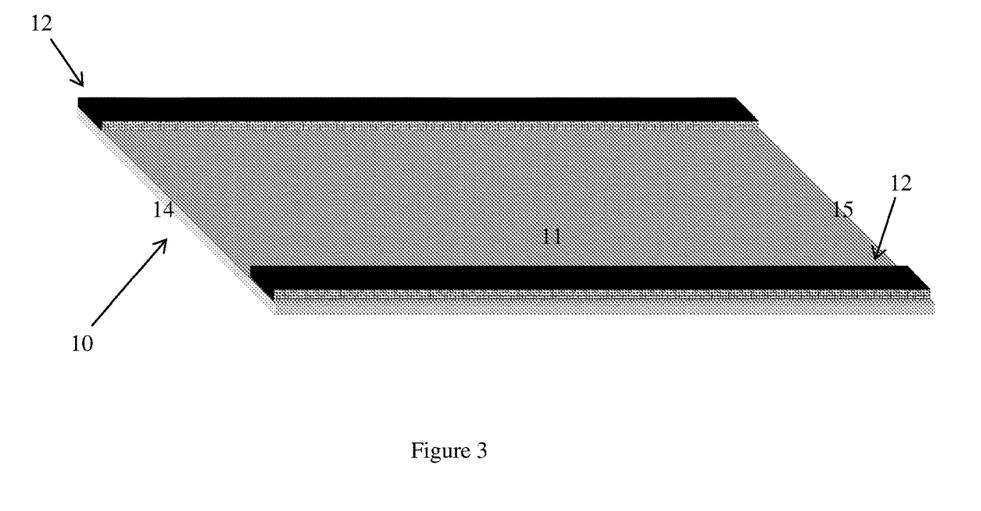
FIG. 3 is an isometric view showing the underside of the therapeutic or play device illustrated in FIG. 2.

As illustrated in FIGS. 1 to 3, the device of the preferred embodiment will typically have an upper side (illustrated in FIG. 1) and a lower side (illustrated in FIG. 2) although the sides are really only defined once the device 10 is attached relative to the surface.

The preferred embodiment includes a substantially planar, resilient, flexible sheet 11 of material. The sheet 11 of material may be any shape although a rectangular shape, as illustrated in FIGS. 1 to 3, is preferred.

The sheet 11 of material may have any size. The particular size of the sheet of material will normally be dependent upon the needs of the user. The sheet of material may be relatively small say approximately 1 m×1 m or may be larger for example between 1 to 2 m in width and 2 to 4 m in length. The different sizes of device will typically provide different functionality. For example, the smaller devices will typically be used to provide a user with sensory feedback from positioning themselves at least partially underneath the device when attached relative to the surface whereas the larger devices may be used for additional purposes such as play beneath the device.

The sheet 11 of material included in the device is typically resilient, preferably resilient in multiple directions. Any suitable material or combination of materials may be used to form the sheet 11. It is particularly preferred that the material used is one or more fabrics. Different materials or surfaces may be provided on the same device. For example, an underside of the sheet of material may be provided in a different configuration to an upper side of the sheet of material in order to provide different sensory feedback on the different sides. One or more different materials may be used over the length of the sheet of material and/or one or more different materials may be used over the width of the sheet of material.

The degree of resilience of the sheet 11 of material may be adjusted or selected through an appropriate choice of material or combination of materials. The material will typically be chosen to provide the required or desired functionality. For example, the main purpose of the device is to provide sensory feedback and therefore, one or more materials may be chosen to provide a particular sensory effect. The material or materials chosen may provide sensory feedback in the form of touch, sight and/or sound or combinations of these particular senses. It is preferred that no sensory effect is provided in terms of smell although this may be possible through an appropriate material choice or through the application of odour materials to the device but particularly not taste. Sensory feedback may be provided in the form of touch by changing the types of materials in terms of surface roughness or finish, for sight the material or materials chosen may have particular visual features either inherent in the manufacture of the materials or applied to the form of shapes or patterns or other visual features and in terms of sound, the materials chosen may make one or more sounds when stimulated such as a ridged material which may make a sound when the user rubs their fingers over it or crinkle paper which makes a crunching sound when touched. Additionally, the type of material and the colour chosen may allow varying degrees of light through the material. These are examples only and any form of material may be provided to achieve a particular sensory effect.

Preferably, the flexible sheet 11 of material is formed from a multidirectional resilient material. In a preferred embodiment, the material is a 20:80 blend of Lycra® and nylon although different blends can and typically will be used to adjust the compression load of the device.

Figure 6:
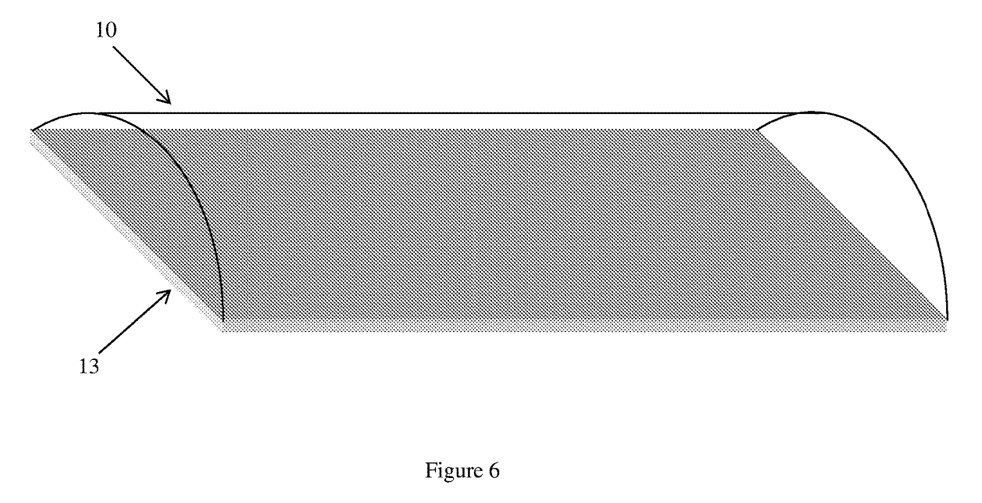
FIG. 6 is an isometric view of an alternative configuration of a therapeutic or play device according to a further preferred embodiment of the present invention.
Figure 7:
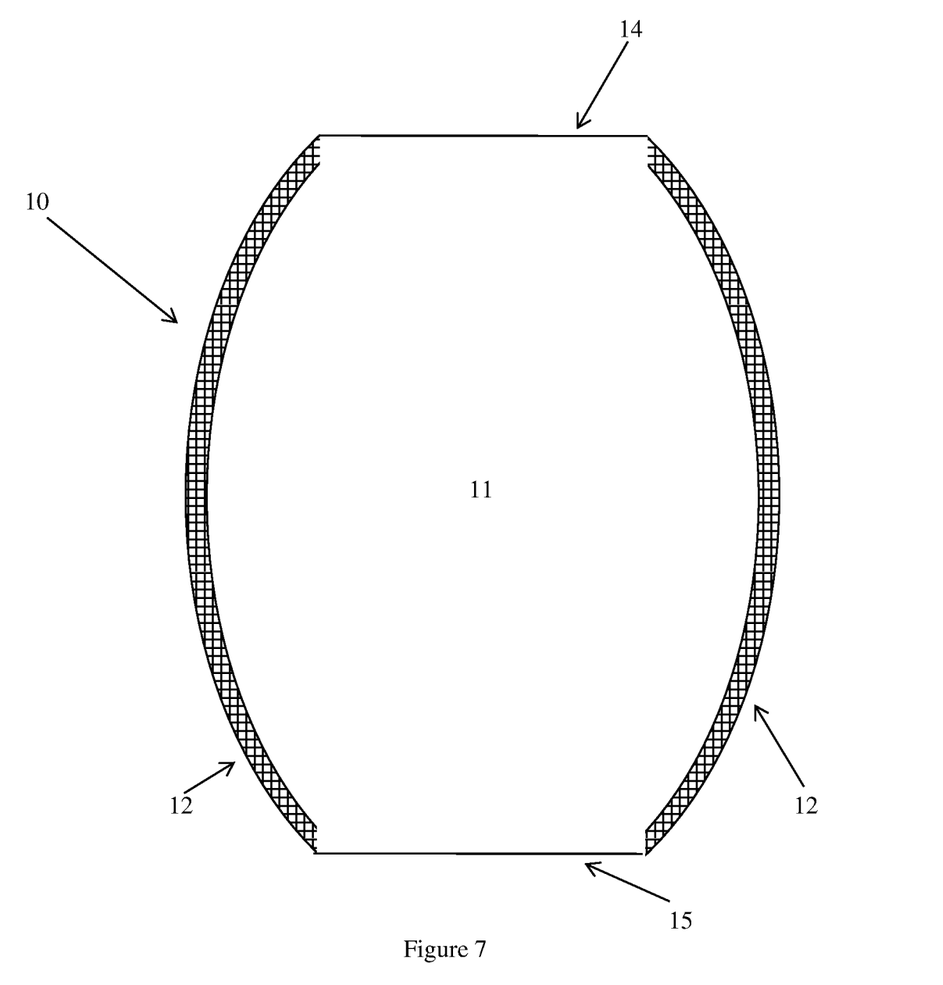
FIG. 7 is a bottom view of a therapeutic or play device according to yet another alternative preferred embodiment.

In a further preferred embodiment, one form of which is illustrated in FIG. 6, a base 13 may be provided relative to which the substantially planar, resilient, flexible sheet 11 of material can be attached. The base 13 may be or provide a surface relative to which the flexible sheet 11 of material can be attached. The base 13 may be configured as a mat for example. The base 13 may have a cushioning effect in order to make the base 13 more comfortable for a user to crawl on or lie on. For example, the base 13 may be formed of a foamed material, a memory foam material or may be inflatable for example. The base 13 may provide a sensory effect or further sensory feedback itself in addition to the flexible sheet 11 of material. In particular, the base 13 may be provided with/chosen for/configured to provide one or more sensory qualities or effects to increase or decrease sensory input for a user.

The base 13 may be provided with one or more attachment mechanisms in order to attach the attachment mechanisms 12 provided on the sheet 11 of material. It is preferred that the base 13 is provided with an attachment mechanism which allows attachment of the preferred sheet 11 of material relative thereto and the attachment mechanism will normally be incorporated into or used on the base 13.

The base 13 may provide the planar sheet 11 of material with the ability to be used both indoors and outdoors. For example, a lower surface of the base 13 may be provided in a waterproof embodiment in order to allow the base 13 to be used on grass.

The base 13 will preferably be generally planar but may be shaped. For example, the base may be or may be provided with shaped blocks or integrated shapes provided on the base or attachable relative thereto which can then be covered by the substantially planar sheet of material.

Any type of attachment mechanism can be used. However, it is preferred that an attachment mechanism which is fast, easy to operate, potentially even with limited tactile skills or grip strength and one which is releasable easily with determined removal but much less easily with accidental removal.

In a particularly preferred embodiment, the attachment mechanism used on the device of the present invention will be a hook portion such as the hook portion from a Velcro fastening system. The hook portion is preferably usable to attach the device relative to floor surfaces such as carpeted floor surfaces. In an alternative embodiment, other systems such as magnets for example may be used but this is not as utilitarian as the hook portion from a Velcro fastening system.

A corresponding portion of the Velcro fastening system, the loop portion may be provided on or relative to the surface. Where the surface is provided as a base 13, the loop portion may be provided on or relative to the base.

Figure 4:
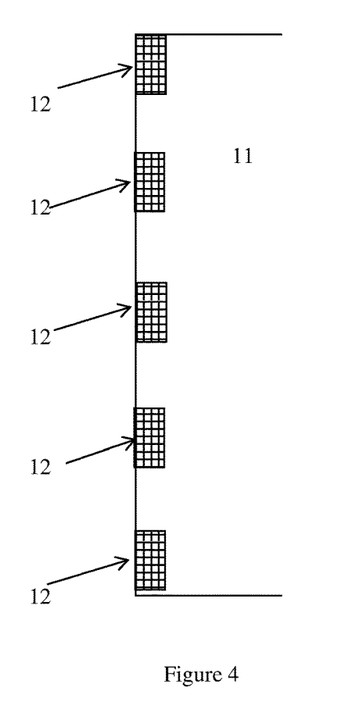
FIG. 4 is a bottom view of a therapeutic or play device as illustrated in FIG. 1 but with an alternative attachment mechanism configuration.
Figure 5:
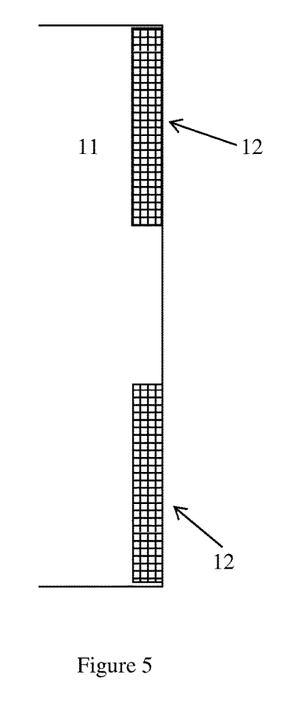
FIG. 5 is a bottom view of the therapeutic or play device as illustrated in FIG. 1 with a further alternative attachment mechanism configuration.

The attachment mechanism extends at least partially along at least a pair of portions. The attachment mechanism may not need to extend continuously along at least a pair of portions and for example, the attachment mechanism may include a number of spaced apart attachment portions such as those illustrated in FIGS. 4 and 5.

It is preferred that the attachment mechanism is provided at or adjacent to a pair of side edges as illustrated in FIGS. 2 and 3 of a substantially rectangular sheet 11 of material but this is not necessarily required. One or more intermediate portions may be provided between an outer pair of attachment portions in order to form "lanes" on the device. An attachment portion may be provided at an end of the preferred embodiment of a substantially rectangular sheet of material but preferably not at both ends as this may create anxiety any user because it may make them feel trapped.

In one preferred embodiment, one or more shaped entryway portions may be provided at an entry/exit of the device in order to hold the entry/exit open for access. Where provided, and entryway portion may have any shape but will preferably be a substantially rigid shape about which a portion of the sheet of material can be preferably releasably attached, such as by using Velcro or similar, in order to hold the entry/exit open, that is, raised above the surface relative to which the device is attached.

In use, the device is fixed to a surface allowing for variability of resistance depending on what is required (less or more resistance). The user can go under it to utilise this resistance or the top side can also be used if the user receives positive sensory feedback from being on the top of it. Primarily its use is for the user to go under between the material and the surface to receive additional proprioceptive input and move, play or lie under it. To begin with the design is that of a tunnel (either rectangle or square shape) with quick release mechanisms, at the moment with a hook/loop attached on either side. It can be sold with or without a base as there are a multitude of common base options e.g. loop carpet tiles can be utilised. It can be positioned horizontally or vertically.

As mentioned above, although the flexible sheet 11 of material may be attached relative to a surface or a base, and in normal use, the flexible sheet 11 will be attached to or relative to a ground surface, preferably a carpeted floor for example.

Educators, therapists, and parents and the like will be able to fulfil the sensory and movement needs of users without being intrusive and without utilising any form of restrictive practice or needing to leave the setting. The user will choose to stay in the space rather than leave the space because they find using the product intrinsically satisfying. When they leave the setting to fulfil their sensory/movement needs it not only creates problems with supervision and safety it is more difficult for the user to return to the setting and they further miss out on being exposed to further knowledge and valuable experiences. By having access to a product that is fixed in the setting it gives the user greater access to the social, communication, education and other benefits of being in that space.

When a Lycra or similar tunnel is used, supervisors and/or facilitators may also hold the ends so that the user can move through it.

The temporarily fixed position of the device provides a multitude of benefits and yet it is easily positioned and it is easily changed or removed. The device of the present invention can be positioned onto any surface and takes up very little space and it is easily positioned and repositioned depending on the users and/or facilitators needs.

The device provides increased proprioceptive input assists in the development of the user's sensory development, sensory motor development, perceptual motor development, cognition and core muscle strength. Users can crawl through the restricted or confined volume improving their reflexive movement/strength or play under it, or simply lie under it.

The amount of resistance placed on the user is dependent upon the amount required by the user/users and can be adjusted quickly and easily. Access to users under the device can be quickly achieve is necessary simply by detachment of the device from the surface, at least partially or fully. In other words, the attachment mechanisms can be moved to make the device either loose on the ground or taut relative to the ground surface, and there may be portions of the device which a loose and then other portions of the device which are taut as required by the user.

It can be used in structured lessons or free play in any number of settings.

It can be used in cooperation with other users or individually.

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

What is claimed is:

1. A therapeutic or play assembly comprising a therapeutic or play device and a planar base, the therapeutic or play device including a substantially planar, multidirectional resilient, flexible sheet of material with a pair of attachment mechanisms, and wherein the pair of attachment mechanisms extend continuously along an entirety of each of a pair of opposed parallel side edges respectively to allow the sheet of material to be attached relative to a surface of the planar base at two spaced apart connection points to form a restricting or confining volume with an entry and an exit at opposed ends of the sheet of material with a resistance applied across the entry and the exit perpendicular to a longitudinal axis of each of the pair of attachment mechanisms, the entry and the exit are elastically deformable requiring at least partial deformation of the sheet of material for entry and exit and wherein the resistance applied is variable across the sheet of material based on a distance between the two spaced apart connection points, wherein at least a portion of an underside of the sheet of material is provided in a different configuration to provide different sensory effect in the form of touch on the underside, wherein one or more materials of construction of the sheet of material are chosen to provide a particular sensory effect in the form of touch, and wherein each of the pair of attachment mechanisms is a hook portion; and the surface of the planar base comprises loop portions reciprocal to the hook portion;

wherein, when the therapeutic or play device is attached to the planar base, the pair of attachment mechanisms and the sheet of material are substantially in the same plane.

2. The therapeutic or play device as claimed in claim 1, wherein the sheet of material is formed from a 20:80 blend of spandex and nylon.

3. The therapeutic or play device as claimed in claim 1, wherein the planar base is provided to be anchored to a surface and relative to which the sheet of material is attached.

4. The therapeutic or play device as claimed in claim 1, wherein one or more shaped entryway portions are provided at an entry/exit of the device in order to hold the entry/exit open for access.

5. The therapeutic or play device as claimed in claim 1, further including one or more holes in the sheet of material.

6. The therapeutic or play device as claimed in claim 1, further including one or more pockets onto the sheet of material in order to allow a user to locate items of educational or intrinsic value.

7. The therapeutic or play device as claimed in claim 1, further including one or more lights or luminescent portions.

8. The therapeutic or play device as claimed in claim 1, further including a cover used over each of the pair of attachment mechanisms to releasably cover each of the pair of attachment mechanisms.

9. A method of using a therapeutic or play device, the therapeutic or play device including a substantially planar, multidirectional resilient, flexible sheet of material with a pair of attachment mechanisms extending continuously along an entirety of each of a pair of opposed parallel side edges respectively, the method comprising:

attaching the sheet of material relative to a surface provided by a planar base having loop portions at two spaced apart connection points to form a restricting or confining volume with an entry and an exit at opposed ends of the sheet of material with a resistance applied across the entry and the exit perpendicular to a longitudinal axis of each of the pair of attachment mechanisms, the entry and the exit are elastically deformable requiring at least partial deformation of the sheet of material for entry and exit and wherein the resistance applied is variable across the sheet of material based on a distance between the two spaced apart connection points, wherein at least a portion of an underside of the sheet of material is provided in a different configuration in order to provide different sensory effect in the form of touch on the underside, and wherein one or more materials of construction of the sheet of material are chosen to provide a particular sensory effect in the form of touch, and wherein each of the pair of attachment mechanisms a hook portion, wherein, when the therapeutic or play device is attached to the planar base, the pair of attachment mechanisms and the sheet of material are substantially in the same plane.

10. The method of using a therapeutic or play device as claimed in claim 9 wherein the pair of attachment mechanisms are provided to allow the device to assume other configurations including a tube, open on both ends.

11. The method of using a therapeutic or play device as claimed in claim 9, wherein more than one therapeutic or play device is attached relative to one another.

12. A therapeutic or play assembly comprising a therapeutic or play device and a planar base, the therapeutic or play device including a substantially planar, multidirectional resilient, flexible sheet of material with a pair of attachment mechanisms, and wherein the pair of attachment mechanisms extend continuously along an entirety of each of a pair of opposed parallel side edges respectively to allow the sheet of material to be attached relative to a surface of the planar base at two spaced apart connection points to form a restricting or confining volume with an entry and an exit at opposed ends of the sheet of material with a resistance applied across the entry and the exit perpendicular to a longitudinal axis of each of the pair of attachment mechanisms, the entry and the exit are elastically deformable requiring at least partial deformation of the sheet of material for entry and exit and wherein the resistance applied is variable across the sheet of material based on a distance between the two spaced apart connection points, wherein at least a portion of an underside of the sheet of material is provided in a different configuration to provide different sensory effect in the form of touch on the underside, wherein one or more materials of construction of the sheet of material are chosen to provide a particular sensory effect in the form of touch, and wherein each of the pair of attachment mechanisms is a hook portion; and the surface of the planar base comprises loop portions reciprocal to the hook portion, and wherein the planar base is entirely planar;

wherein, when the therapeutic or play device is attached to the planar base, the pair of attachment mechanisms and the sheet of material are substantially in the same plane.

* * * * *